United States Patent
Ng

(10) Patent No.: US 9,380,779 B2
(45) Date of Patent: Jul. 5, 2016

(54) AQUEOUS COMPOSITION FOR ACCELERATING SECRETION OF ALPHA-AMYLASE IN PLANT SEED GERMINATION

(75) Inventor: Denny Ng, Walnut, CA (US)

(73) Assignee: Loveland Products, Inc., Loveland, CO (US)

( * ) Notice: Subject to any disclaimer, the term of this patent is extended or adjusted under 35 U.S.C. 154(b) by 173 days.

(21) Appl. No.: 13/592,136

(22) Filed: Aug. 22, 2012

(65) Prior Publication Data
US 2013/0047505 A1     Feb. 28, 2013

Related U.S. Application Data

(60) Provisional application No. 61/527,488, filed on Aug. 25, 2011.

(51) Int. Cl.
| | |
|---|---|
| A01C 1/06 | (2006.01) |
| A01N 37/40 | (2006.01) |
| A01C 1/02 | (2006.01) |
| A01N 33/12 | (2006.01) |
| A01N 43/08 | (2006.01) |
| A01N 43/16 | (2006.01) |
| A01N 43/38 | (2006.01) |

(52) U.S. Cl.
CPC . *A01N 37/40* (2013.01); *A01C 1/02* (2013.01); *A01N 33/12* (2013.01); *A01N 43/08* (2013.01); *A01N 43/16* (2013.01); *A01N 43/38* (2013.01)

(58) Field of Classification Search
CPC ............ A01C 1/025; A01C 1/02; A01C 1/00; A01C 1/06
USPC ................ 47/58.1 SE, 58.1 R, 57.6, DIG. 91; 504/138, 100, 14, 284, 299; 514/415
See application file for complete search history.

(56) References Cited

U.S. PATENT DOCUMENTS

| | | | |
|---|---|---|---|
| 4,799,950 | A | 1/1989 | Suzuki et al. |
| 4,978,381 | A | 12/1990 | Hadwiger |
| 5,006,149 | A | 4/1991 | Kiss et al. |
| 5,201,931 | A | 4/1993 | Abrams et al. |
| 5,298,482 | A | 3/1994 | Tanaka et al. |
| 6,114,603 | A | 9/2000 | Christon et al. |
| 6,455,468 | B1 | 9/2002 | Li et al. |
| 7,740,680 | B2 | 6/2010 | Marks |
| 2003/0224936 | A1 | 12/2003 | Kretzschmar |
| 2004/0035162 | A1 | 2/2004 | Williams et al. |
| 2004/0259732 | A1 | 12/2004 | Asrar et al. |

FOREIGN PATENT DOCUMENTS

| | | |
|---|---|---|
| CN | 1328769 A | 1/2002 |
| CN | 102267935 B | 12/2011 |
| WO | WO2010116259 A2 | 10/2010 |

OTHER PUBLICATIONS

Freytag, A.H. et al., "An improved medium for adventitious shoot formation and callus induction in *Beta vulgaris* L. in vitro", Plant Cell Reports, 1988, No. 7, pp. 30-34.

(Continued)

*Primary Examiner* — Trinh Nguyen
(74) *Attorney, Agent, or Firm* — Faegre Baker Daniels LLP

(57) ABSTRACT

A seed treatment composition includes ascorbic acid, choline chloride, indole-3-butyric acid, and water. In some embodiments, the seed treatment composition may further include salicylic acid.

19 Claims, 1 Drawing Sheet

(56) References Cited

OTHER PUBLICATIONS

International Search Report and Written Opinion issued in PCT/US12/51928, mailed Mar. 18, 2013, 10 pages.

Kato-Noguchi, Hisashi, "Effects of four benzoxazinoids on gibberellins-induced alpha-amylase activity in barley seeds", Journal of Plant Physiology, vol. 165, 2008, pp. 1889-1894.
Van, Le Bui, Part II, Plant tissue Culture (Oreview), Presentation Apr. 2009, Plant Biotechnology, Vietnam OpenCourseWare, 84 pages.
European Search Report issued in EP Application No. 12825778.9, mailed Apr. 8, 2015, 5 pages.

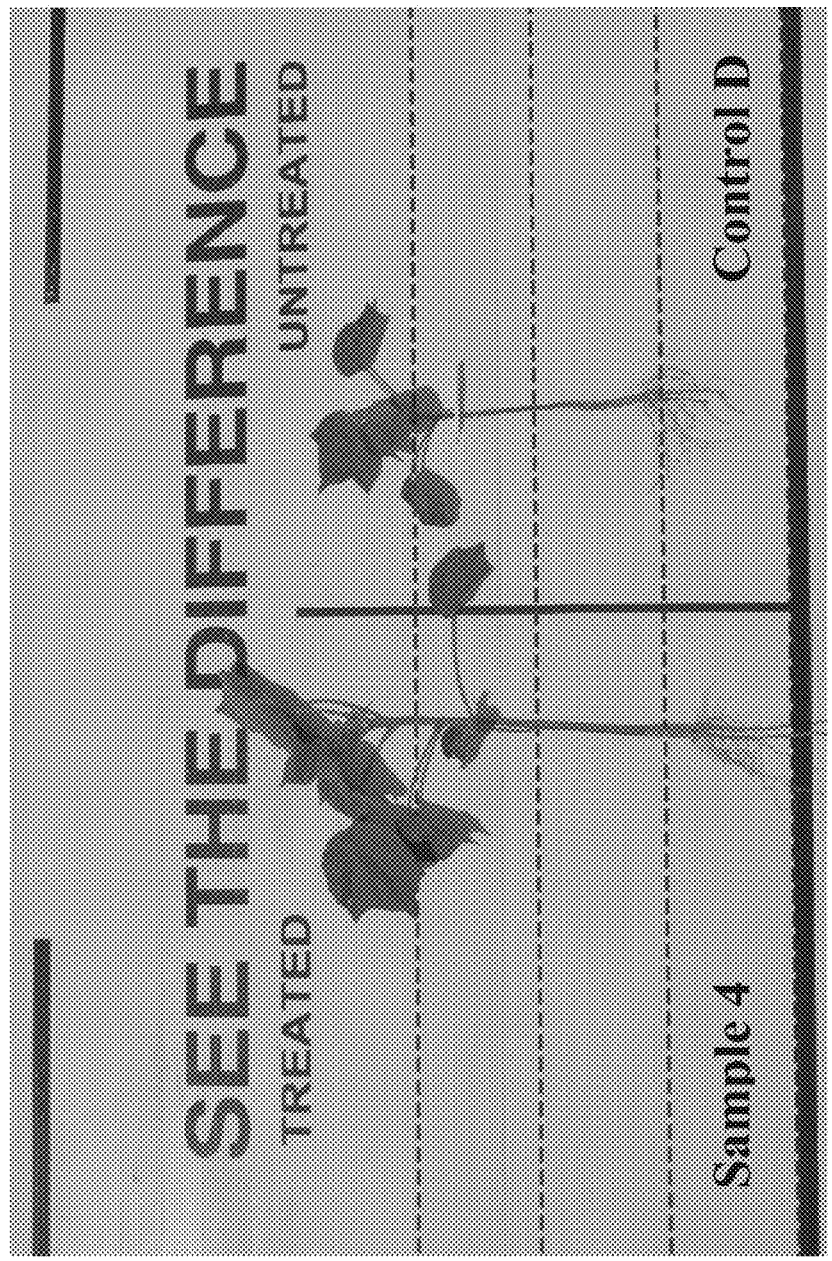

AQUEOUS COMPOSITION FOR ACCELERATING SECRETION OF ALPHA-AMYLASE IN PLANT SEED GERMINATION

CROSS-REFERENCE TO RELATED APPLICATION

This application claims priority to Provisional Patent Application No. 61/527,488, filed Aug. 25, 2011, which is herein incorporated by reference in its entirety.

TECHNICAL FIELD

The present invention relates to a seed treatment composition for producing strong and healthy seedlings. More particularly, the present invention relates to a seed treatment composition including ascorbic acid, choline chloride, and indole-3-butyric acid.

BACKGROUND

Seed germination is the growth of an embryonic plant contained within the seed, which emerges as a seedling having roots and shoots. Seed germination is the first critical phase in plant growth and development, and establishment of strong and healthy seedlings typically results in a higher yield crop production.

Seeds of most plant species contain an embryo and some store of food reserves. In seed germination, the food reserves are hydrolyzed (digested) by enzymes to provide substrates for energy as well as blocks of macromolecules for the emergence of shoots from the soil. The majority of the food reserve in the seed is starch, which is digested into sugar mainly by the catalyst of α-amylase.

Gibberellins have been used to trigger starch hydrolysis through inducing α-amylase synthesis in the aleurone cells. It has been demonstrated that gibberellins produced in the scutellum diffuse to the aleurone cells where they cause higher levels of transcription of the gene coding α-amylase and stimulate the secretion of α-amylase.

However, gibberellins also stimulate the elongation of the shoots by stimulating cell division and elongation. Application of exogenous gibberellins typically result in slender seedlings having weak steams that fall over easily and are less resistant to stresses such as drought, cold, heat, salt, flooding, and pathogen attacks. Gibberellin molecules may also be difficult to incorporation into stable products because they are typically unstable and may easily decompose in water.

SUMMARY

The present invention includes a seed treatment composition for the establishment of strong and healthy seedlings. The seed treatment composition can include ascorbic acid, choline chloride, and indole-3-butyric acid. The seed treatment composition can additionally include salicylic acid.

In one embodiment, the seed treatment composition includes between about 0.001% and about 2% ascorbic acid, between about 0.001% and about 1.5% choline chloride, and between about 0.00001% and about 0.5% indole-3-butyric acid by weight of the composition.

A method of treating seeds with the seed treatment composition is also provided.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a photographic image comparing a plant treated with a seed treatment composition and a plant not treated with a seed treatment composition.

DETAILED DESCRIPTION

Embodiments of the present invention provide seed treatment compositions useful for treating seeds of a variety of plants, such as but not limited to, corn, wheat, barley, rice, soybean, cucumber, cotton, lettuce, pepper, and watermelon. Embodiments of the present invention can accelerate α-amylase synthesis and secretion in seed germination, promoting mobilization of seed reserved starch and increasing the chemical energy and substrates necessary for the emergence of roots and shoots. Increased alpha-amylase (α-amylase) synthesis and secretion may lead to establishment of strong seedlings which are fast growing and have strong resistance against stresses, such as drought, cold, and heat.

The seed treatment composition generally includes ascorbic acid, choline chloride, indole-3-butyric acid and optionally salicylic acid. Ascorbic acid (or its salt form ascorbate) is a major metabolite in plants. It is an antioxidant that protects plants against oxidative damage resulting from aerobic metabolism, photosynthesis, and a range of pollutants. Ascorbic acid is a cofactor for some hydroxylase enzymes and violaxanthin de-epoxidase. It is present in the cell wall where it is the first line of defense against ozone and acts to control cell division and growth. Exogenous application of ascorbic acid simulates embryo cell division and active gibberellins biosynthesis necessary for α-amylase secretion. Ascorbic acid also causes a weak acid environment favorable to α-amylase secretion and function. Ascorbic acid may also be present as a salt (e.g., sodium, calcium or potassium ascorbate), or as a fatty acid ester (e.g., ascorbyl palmitate or ascorbyl stearate).

The seed treatment composition also includes choline chloride. Choline chloride $((CH_3)_3N(Cl)CH_2CH_2OH)$ protects cell membranes in plants, which is particularly important in order for plants to grow and survive under various environmental conditions. Young seedlings are typically weak and sensitive to environmental changes. Choline chloride may stabilize the membrane and biochemical metabolism during seed germination.

The seed treatment composition further includes indole-3-butyric acid. Indole-3-butyric acid is a plant hormone in the auxin family that has shown many regulatory effects in plants, such as but not limited to, cell division, rooting, shape formation, light and gravity tropism, and fruit and seed formation. Indole-3-butyric acid may also promote the amount of active gibberellins in plant tissues. During seed germination, indole-3-butyric acid may also stimulate division of embryo cells, growth of roots and shoots, and gibberellins biosynthesis for the induction of α-amylase.

The seed treatment composition may optionally further include salicylic acid. It has been found that salicylic acid $(C_7H_6O_3)$ may function as a plant hormone. Salicylic acid can also enhance cell resistance to pathogens and other stresses such as cold, heat and salt. Salicylic acid may also be present as a salt, such as salicylates.

The seed treatment composition can be an aqueous solution comprising water as a diluent. As described further below, the seed treatment composition can be provided as a concentrate solution or as a ready to use solution. The ready to use solution contains more water than the concentrate solution. In one example, the seed treatment composition is a clear aqueous solution. In one embodiment, the concentrate or ready to use solution may include from about 0.001 to about 2% by weight ascorbic acid, from about 0.001 to about 1.5% by weight choline chloride, from about 0.00001 to about 0.5% by weight indole-3-butyric acid and optionally, from about 0.001 to about 1.0% by weight salicylic acid.

In another embodiment, the concentrate solution may include from about 0.05 to about 1.5% by weight ascorbic acid, from about 0.005 to about 1.0% by weight choline chloride, from about 0.001 to about 0.1% by weight indole-3-butyric acid and optionally, from about 0.001 to about 0.5% by weight salicylic acid.

In a further embodiment, the ready to use solution may include from about 0.005 to about 1.0% by weight ascorbic acid, from about 0.005 to about 0.5% by weight choline chloride, from about 0.0001 to about 0.03% by weight indole-3-butyric acid and optionally, from about 0.0005 to about 0.03% by weight salicylic acid.

In a still further embodiment, the ready to use solution may include from about 0.025 to about 0.1% by weight ascorbic acid, from about 0.015 to about 0.06% by weight choline chloride, from about 0.001 to about 0.004% by weight indole-3-butyric acid and optionally, from about 0.0005 to about 0.03% by weight salicylic acid.

The seed treatment composition may include additional function ingredients such as, but not limited to, stability agents, surfactants, inorganic or polymeric thickeners, penetrating and retaining agents, antifoaming agents, antifreezes, preservatives, sequestrants, dyes and odorants, buffering agents, solvents, and additional plant growth regulators, anti-microbial, anti-bacterial and/or anti-fungal agents.

Dyes can be added to the seed treatment composition in order to make it easier to identify seeds treated with the seed treatment composition. Dyes may also be added to the seed treatment composition for aesthetic purposes. Odorants can be added to the seed treatment composition to improve the odor of the composition.

The seed treatment composition has an acidic pH. In one example, the seed treatment composition has a pH of less than about 4.0 in its ready to use form. In another example, the seed treatment composition has a pH of less than 3.7. In a further example, the seed treatment composition has a pH of 3.5 or less. A buffering agent may be used to adjust the pH of the seed treatment composition and/or prevent a change in pH. Monobasic potassium phosphate is one example of a buffering agent. Monobasic potassium phosphate has a mildly acidic reaction, and functions to minimize pH fluctuations when used with urea or diammonium phosphate.

As discussed above, the seed treatment composition can be a clear solution. Solvents can be added to the seed treatment composition to assist in dissolving components of the seed treatment composition. Example solvents include choline chloride, urea, and citric acid.

Additional plant growth regulators, anti-microbial, anti-bacterial and/or anti-fungal agents include but are not limited to brassinolides such as epibrassinolides, indoleacetic acid preparations, ethychlozate preparations, 1-naphthylamide preparations, isoprothiolane preparations, nicotinic acid amide preparations, hydroxyisoxasole preparations, calcium peroxide preparations, benzylaminopurine preparations, methasulfocarb preparations, oxyethylene docosanol preparations, ethephon preparations, cloxyfonac preparations, gibberellin, streptomycin preparations, daminozide preparations, 4-CPA preparations, ancymidol preparations, inabenfide preparations, uniconazole preparations, chlormequat preparations, dikegulac preparations, daminozide preparations, mefluidide preparations, calcium carbonate preparations, piperonyl butoxide preparations, and chitosan.

The current seed treatment composition may be applied to seeds prior to sowing to improve the health and strength of the resulting seedlings. The current seed treatment composition can be applied to seeds of various plants, such as but not limited to, corn, wheat, barley, rice, soybean, cucumber, cotton, lettuce, pepper, and watermelon. When treating seeds with the current seed treatment composition, the seeds are contacted with the composition prior to sowing the seeds. The seeds may be treated using a batch process or a continuous process. Contacting seeds with the composition can include coating the seeds or soaking the seeds in the seed treatment composition. For example, the seeds can be sprayed, coated or mixed with the liquid seed treatment composition. Some seeds may be sensitive to moisture, and soaking of such seeds for extended periods of time may not be desirable.

The seed treatment composition can be provided as a concentrate solution or as a ready to use solution. A concentrate solution refers to a solution which is intended to be diluted with water to form a use solution prior to contact with seeds. A ready to use solution is not diluted with water prior to contact with seeds. A ready to use solution is a use solution when it is applied to seeds without further dilution. A suitable application rate of the use solution is between about 0.033 grams to about 1.0 gram of use solution per 100 pounds of seed.

Suitable concentration ranges for the concentrate seed treatment composition are provided in Table 1 and suitable concentration ranges for the ready to use seed treatment composition are provided in Table 2. In some embodiments, the concentrate seed treatment composition and ready to use seed treatment composition can consist of or consist essentially of the components listed in Tables 1 and 2 respectively.

TABLE 1

Suitable concentrate seed treatment compositions

| Component | First example range (wt %) | Second example range (wt %) | Third example range (wt %) |
|---|---|---|---|
| L-ascorbic acid | 0.001-2 | 0.05-1.5 | 0.1-1 |
| Choline chloride | 0.001-1.5 | 0.005-1.0 | 0.01-0.5 |
| Indole-3-butyric acid | 0.00001-0.5 | 0.001-0.1 | 0.005-0.5 |
| Salicylic acid | 0.001-1 | 0.001-0.5 | 0.01-0.1 |
| Chitosan | 0.005-10 | 0.01-7 | 0.5-5 |
| Water | 75-99.99 | 85-99.99 | 90-99.99 |
| Buffer | 0.001-2 | 0.05-1.5 | 0.1-1 |
| Solvent | 0.005-3.5 | 0.5-3.0 | 1-2.5 |

TABLE 2

Suitable ready to use seed treatment compositions

| Component | First example range (wt %) | Second example range (wt %) | Third example range (wt %) | Fourth Example range (wt %) |
|---|---|---|---|---|
| L-ascorbic acid | 0.001-2 | 0.005-1.0 | 0.01-0.5 | 0.025-0.1 |
| Choline chloride | 0.001-1.5 | 0.005-0.5 | 0.01-0.1 | 0.015-0.06 |

TABLE 2-continued

Suitable ready to use seed treatment compositions

| Component | First example range (wt %) | Second example range (wt %) | Third example range (wt %) | Fourth Example range (wt %) |
|---|---|---|---|---|
| Indole-3-butyric acid | 0.00001-0.5 | 0.0001-0.03 | 0.0005-0.01 | 0.001-0.004 |
| Salicylic acid | 0.001-1.0 | 0.0005-0.03 | 0.001-0.03 | 0.001-0.03 |
| Chitosan | 0.005-10 | 0.01-2.0 | 0.05-1.5 | 0.05-1.5 |
| Water | 75-99.99 | 85-99.99 | 90-99.99 | 90-99.99 |
| Buffer | 0.001-2 | 0.005-1.0 | 0.01-0.5 | 0.01-0.5 |
| Solvent | 0.005-3.5 | 0.01-1.5 | 0.05-1 | 0.05-1 |

The concentrate seed treatment composition can be formed by mixing the ingredients together to form a solution. In one example, indole-3-butyric acid can be pre-dissolved with ethyl alcohol before mixing with the other ingredients. The concentrate seed treatment composition may be diluted with water to form a use solution having a suitable concentration of ingredients.

One of the important events during early germination is the synthesis of new proteins of hydrolase. Among the newly synthesized proteins, α-amylase typically accounts for the largest percentage. α-amylase is a key enzyme catalyzing the breakdown of starch into glucose and supplying chemical energy for the emergence of seedlings. More specifically, α-amylase is an endo-α-1,4-glucanase, which breaks the glucan backbone in amylase and amylopecin, and provides oligomers for further action by β-amylase. The current seed treatment composition has demonstrated remarkable stimulation of embryo cell division and α-amylase secretion, leading to the establishment of healthy seedlings with strong resistance to various stresses. It has been found that when ascorbic acid, choline chloride, indole-3-butyric acid and salicylic acid are combined in the present seed treatment composition, the plant growth regulating actions of the respective components are increased synergistically, and the combination of the components exhibits a marked synergistic effect not seen when the components are used individually.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Seed Treatment Composition Formulation

A concentrate seed treatment composition was formed by adding 600 ml of water to a 1000 ml beaker. Five grams ascorbic acid followed by 3 grams choline chloride were added to the 1000 ml beaker and stirred until fully dissolved. Then, 0.2 grams indole-3-butyric acid (pre-dissolved with 5 ml 95% ethyl alcohol) was added to the 1000 ml beaker and stirred until it was a clear solution. Finally, water was added to the solution to a total volume of 1000 ml. To form a use solution for contact with the seeds, the concentrate seed treatment composition was diluted to 10 times with water.

Seed Treatment and Culturing

To treat and culture seeds, the seeds were soaked in the seed treatment composition use solution described above for four hours. The seeds were soaked in 10 ml of seed treatment composition use solution per 10 grams of seeds. The seeds were cultured in Petri dishes for germination at 25° C. in a plant growth chamber. Seeds soaked in water for the same time period as those soaked in the seed treatment composition were used as a control. The activity of α-amylase was measuring according to the extraction and assay of α-amylase method below in 24 hour increments from 24 to 96 hours after the soaking period.

Extraction and Assay of α-Amylase

The method used for extraction and assay of α-amylase activity is described in Hisashi Kato-Noguchia and Francisco A. Macias, Effects of Four Benxoxazinoids on Gibberellin-Induced α-Amylase Activity in Barley Seeds, Journal of Plant Physiology 165 (2008): 1889-1894. First, seeds were freeze-dried. The freeze-dried seeds (10 seeds for one determination) were ground to a fine powder in a mortar using a pestle. The powder was then homogenized with an ice-cold solution of 100 mmol/L HEPES-KOH (pH 7.5) containing 1 mmol/L EDTA, 5 mmol/L $MgCl_2$, 5 mmol/L DDT, 10 mmol/L $NaHSO_3$ and 50 mmol/L bovine serum albumin. The corn, soybean and cucumber seeds were mixed with 1.5 ml of the ice-cold solution per seed, and the wheat, barley and rice seeds were mixed with 0.5 ml of the ice-cold solution per seed. The homogenate was centrifuged at 30,000 g for 30 minutes, and the supernatant was heated with 3 mmol/L $CaCl_2$ at 75° C. for 15 minutes to inactivate β-amylase and α-glucosidase. This heat-treated supernatant was used for α-amylase assay.

The α-amylase was assayed by measuring the rate of generation of reducing sugars from soluble starch. 0.2 mL of the heat-treated supernatant was added to 0.5 mL of 100 mmol/L Na-acetate (pH 6.0) containing 10 mmol/L $CaCl_2$. Reaction was initiated with 0.5 mL 2% (w/v) soluble starch. After incubation at 37° C. for 15 minutes, the reaction was terminated by adding 0.5 mL of 40 mmol/L dinitrosalicylic acid solution containing 400 mmol/L NaOH and 1M K—Na tartrate, and then placing immediately into a boiling water bath for 5 minutes. After dilution with distilled water, the $A_{530}$ of the reaction mixture was measured and the reducing power was evaluated using a standard curve obtained with glucose. Table 3 provides the α-amylase activity (in mmol $min^{-1}$ $mg^{-1}$ protein) at 24 hours, 48 hours, 72 hours and 96 hours after soaking in either the seed treatment composition (treated) or water (control).

TABLE 3

| | | α-amylase activity (mmol $min^{-1}$ $mg^{-1}$ protein) | | | |
|---|---|---|---|---|---|
| Seed | Treatment | 24 hours | 48 hours | 72 hours | 96 hours |
| Corn | Treated | 376 + 42 | 857 ± 37 | 1941 ± 67 | 2136 + 58 |
| | Control | 215 ± 26 | 646 ± 32 | 1526 ± 52 | 1683 ± 66 |
| Wheat | Treated | 297 ± 27 | 806 ± 42 | 1638 ± 73 | 2211 ± 82 |
| | Control | 221 ± 24 | 544 + 36 | 985 ± 49 | 1492 + 65 |
| Barley | Treated | 265 ± 33 | 961 ± 56 | 1839 ± 94 | 2417 ± 115 |
| | Control | 185 ± 35 | 603 ± 47 | 863 ± 74 | 1383 ± 92 |
| Rice | Treated | 102 ± 16 | 427 ± 36 | 1124 ± 64 | 1869 ± 75 |
| | Control | 64 ± 13 | 275 ± 28 | 635 ± 39 | 967 ± 56 |
| Soybean | Treated | 81 ± 14 | 268 ± 36 | 763 ± 66 | 1328 ± 97 |
| | Control | 67 ± 17 | 176 ± 27 | 521 ± 58 | 769 ± 73 |
| Cucumber | Treated | 185 ± 26 | 452 ± 56 | 1013 ± 85 | 1834 ± 112 |
| | Control | 83 ± 24 | 294 ± 52 | 736 ± 69 | 1048 ± 86 |

As shown in Table 3, seeds treated with the seed treatment composition (treated) had higher α-amylase activity than seeds treated with water (control).

In Table 3, the seeds were treated with a use solution that was a 10 times dilution of the concentrate seed treatment composition. Additional experiments treated corn, wheat, barley, rice, soybean and cucumber seeds with a use solution have a 5-20 times dilution of the concentrated seed treatment composition. These seeds showed an increased α-amylase activity compared to seeds treated with water. Further experiments treated corn, wheat, barley, rice, soybean and cucumber seeds with a use solution have a 1-3 times dilution of the concentrated seed treatment composition. These seeds showed an inhibited α-amylase activity compared to seeds treated with water. Still further experiments treated corn, wheat, barley, rice, soybean and cucumber seeds with a use solution have a greater than 20 times dilution of the concentrated seed treatment composition. These seeds showed little increase in α-amylase activity compared to seeds treated with water.

Field Testing

The seed treatment composition of the current disclosure was applied to various crop seeds. The seeds were planted or sowed in test plots located in the United States using appropriate agricultural planting equipment. The plants were observed and evaluated over one growing season.

Plant density was determined at a specified number of days after planting by counting the number of plants in the test plot. Plant density is typically expressed as number of plants per row foot (e.g., per foot of a crop row). Previous research has shown that 6-7 soybean plants per row foot is optimal for maximum yield production.

Average plant height is determined by measuring the height of a representative sample of plants in the test plot a specified number of days after planting. A higher average plant height may be a good indicator of overall early plant health and development.

Shoot biomass and root biomass are determined by randomly selecting and removing a representative number of plants from the test plot. The entire plant is removed by digging the plant from the soil. The plants are washed to remove any soil from the roots, the above ground portion of the plant (shoots) are removed from the roots. The shoots and roots are weighted separately to determine the average shoot biomass and the average root biomass, respectively. A higher shoot biomass may be viewed as a positive characteristic of a healthy, well developing plant. A higher root biomass may also be viewed as a positive characteristic of a health, well developing plant. The shoot biomass and root biomass may be determined early during plant development, such as at 50 days after planting. A higher root biomass during early plant development may be more efficient in utilizing available soil moisture and soil nutrients. Additionally, a plant with a higher root biomass may recover from early stress or damage from frost or herbicides faster and more efficiently.

A grain moisture rating is determined at harvest with a commercially available gain moisture meter. The grain moisture rating at harvest may be an indicator of the relative maturity of a plant. A high moisture rating may indicate that the plant is less developed and can result in poor test weight, less protein and feed value, and be a storage issue (e.g., it may require additional drying to prevent mold and/or a decline in quality and value.) An extremely low moisture value may also indicate a poor quality crop and an extremely low moisture crop may break or shatter during harvest.

Soybean Field Test

Soybeans seed treated with the seed treatment composition of the current disclosure were compared to soybeans seed that were not treated with seed treatment composition. Prior to planting, the soybeans of Sample 1 were treated with a commercially available insecticide/fungicide seed treatment and then were treated with the seed treatment of Table 4 at a rate of 0.4 ounces per 100 pounds of seed (oz/cwt).

TABLE 4

| Component | Amount (% wt) |
| --- | --- |
| L-ascorbic acid | 0.083 |
| Choline chloride | 0.05 |
| Indole-3-butyric acid | 0.003 |
| Salicylic acid | 0.007 |
| Chitosan | 0.17 |
| Water | Balance |
| Buffer | 0.08 |
| Solvent | 0.31 |

The soybeans of Control A and Control B were of the same variety as those of Sample 1. The soybeans of Control A were treated with same commercially available insecticide/fungicide seed treatment as Sample 1 but were not treated with the seed treatment of the current disclosure. The soybeans of Control B were not treated with the commercially available insecticide/fungicide seed or the seed treatment of the current disclosure.

The soybeans of Sample 1, Control A and Control B were planted in a test plot using the same planting parameters (e.g., spacing) and were subject to the same environmental conditions. Table 5 summarizes the plant density at 21 days after planting (21 DA-P); the plant density, average plant height, root biomass, and shoot biomass 43 days after planning (43 DA-P); and the grain moisture rating at harvest, 150 days after planting (150 DA-P), for Sample 1, Control A and Control B.

TABLE 5

|  | Sample 1 | Control A | Control B |
| --- | --- | --- | --- |
| Plant density (21 DA-P) (plants per row foot) | 5.7 | 4.7 | 5.6 |
| Plant density (43 DA-P) (plants per row foot) | 5.7 | 4.7 | 5.6 |
| Average plant height (43 DA-P) (inches) | 11.3 | 10.8 | 10.5 |
| Average root biomass (43 DA-P) (grams) | 10.6 | 11.9 | 11.1 |
| Average shoot biomass (43 DA-P) (grams) | 49.2 | 48.1 | 42.4 |
| Grain moisture rating (150 DA-P) (weight percent moisture) | 9.2 | 10.2 | 9.3 |

The plant density for Sample 1 was the same 21 days and 43 days after planting, which indicates that the plants emerged strong and there was no loss of plants between day 21 and day 43. Additionally, Sample 1 had a higher plant density than Control A and Control B and was closer to the optimal 6-7 soybean plants per row foot.

Forty-three days after planting, the average plant height, root biomass and shoot biomass were determined. Sample 1 had a greater average plant height and average shoot biomass value than Control A and Control B, suggesting that plants of Sample 1 were healthier and better developed than those of Control A and Control B.

Sample 1 had a lower root biomass than Control A and Control B. Taken together with the shoot biomass value, it appears that the plants of Sample 1 directed more mass growth to the shoots than to the roots as compared to Control A and Control B.

The grain moisture rating was determined 150 days after planting. As shown in Table 5, Sample 1 had a lower percent moisture than Control A and a slightly lower percent moisture than Control B. This suggests that the plants of Sample 1 were more mature than those of Control A and Control B, allowing the plants of Sample 1 to be suitable for harvest prior to those of Control A.

Cotton Field Test—Sample 2 and Control C

Cotton seed treated with the seed treatment of the present disclosure was compared to cotton seed not treated with the seed treatment of the present disclosure. Prior to planting, the seeds of Sample 2 were treated with a commercially available nematicide seed treatment and then were treated with the seed treatment of Table 4 at a rate of 0.4 ounces per 100 pounds of seed (oz/cwt). The seeds of Control C were of the same variety as those of Sample 2. The seeds of Control C were treated with same commercially available nematicide seed treatment as Sample 2 but were not treated with the seed treatment of the current disclosure.

The shoot biomass and root biomass 28 days after planting were measured for each sample. The yield at harvest was also determined.

TABLE 6

|  | Sample 2 | Control C |
|---|---|---|
| Average shoot biomass (28 DA-P) Grams/20 plants | 132 | 140 |
| Average root biomass (28 DA-P) Grams/20 plants | 20.3 | 19.5 |
| Yield (lbs/acre) | 1642 | 1576 |

Sample 2 had a lower shoot biomass and a higher root biomass than Control C. At harvest, Sample 2 had a larger yield than Control C. The higher root biomass of Sample 2 appears to have resulted in a more developed and higher quality grain, resulting in a higher yield at harvest.

Sample 4 and Control D

Cotton seed treated with the seed treatment of the present disclosure was compared to cotton seed not treated with the seed treatment of the present disclosure. Prior to planting, the seeds of Sample 4 were treated with the seed treatment of Table 4 at a rate of 0.8 ounces per 100 pounds of seed (oz/cwt). The seeds of Control D were of the same variety as those of Sample 4 but were not treated with the seed treatment of Table 4.

A representative plant of Sample 4 and Control D were removed from the test plot 14 days after emergence. A photographic image of the plants is presented in FIG. 1. As shown, the cotton plant of Sample 4 was taller above ground and had a larger number of leaves than Control D. Additionally, the roots of Sample 4 were longer, suggesting that the roots of Sample 4 extended deeper into the ground than those of Control D.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A ready to use seed treatment composition comprising:
   between about 0.025% to about 0.10% ascorbic acid by weight of the seed treatment composition;
   between about 0.015% and about 0.060% choline chloride by weight of the seed treatment composition;
   between about 0.001% and about 0.004% indole-3-butyric acid by weight of the seed treatment composition; and
   water.

2. The ready to use seed treatment composition of claim 1, and further comprising between about 0.001% and about 0.03% salicylic acid by weight of the seed treatment composition.

3. The ready to use seed treatment composition of claim 1, and further comprising at least one solvent selected from the group consisting of: urea and citric acid.

4. The ready to use seed treatment composition of claim 1, and further comprising at least one buffer.

5. The ready to use seed treatment composition of claim 1, wherein the seed treatment composition has a pH of less than about 4.0.

6. The ready to use seed treatment composition of claim 1, and further comprising an anti-fungal agent in an amount between about 0.05% and about 1.5% by weight of the ready to use seed treatment and wherein the anti-fungal agent comprises chitosan.

7. The ready to use seed treatment composition of claim 1, wherein the seed treatment composition consists essentially of:
   the ascorbic acid;
   the choline chloride;
   the indole-3-butyric acid;
   salicylic acid;
   at least one anti-fungal agent;
   at least one solvent;
   at least one buffer; and
   the water.

8. A seed treatment composition comprising:
   between about 0.025% and about 0.10% ascorbic acid by weight of the composition;
   between about 0.015% and about 0.06% choline chloride by weight of the composition; and
   between about 0.001% and about 0.004% indole-3-butyric acid by weight of the composition.

9. The seed treatment composition of claim 8, further comprising:
   between about 0.001% and about 1% salicylic acid by weight of the composition.

10. The seed treatment composition of claim 8, wherein the composition further comprises:
    between about 0.01% and about 0.1% salicylic acid by weight of the composition; and
    between about 90% and about 99.99% water by weight of the composition.

11. The seed treatment of claim 8, wherein the seed treatment consists essentially of:
    the ascorbic acid;
    the choline chloride;
    the indole-3-butyric acid;
    salicylic acid;
    at least one buffer;
    at least one solvent;
    water; and
    at least one anti-fungal agent.

12. The ready to use seed treatment composition consisting essentially of:

ascorbic acid between about 0.025% to about 0.10% by weight of the seed treatment composition;
choline chloride between about 0.015% and about 0.060% by weight of the seed treatment composition;
indole-3-butyric acid between about 0.001% and about 0.004% by weight of the seed treatment composition;
salicylic acid;
a solvent;
a buffer;
an anti-fungal agent; and
water.

13. The ready to use seed treatment composition of claim 12, wherein the salicylic acid is between about 0.001% and 0.03% by weight of the seed treatment composition.

14. The ready to use seed treatment composition of claim 12, wherein the solvent is selected from the group consisting of urea, citric acid, and a mixture of urea and citric acid.

15. The ready to use seed treatment composition of claim 14, wherein the solvent is between 0.05% and 1% by weight of the seed treatment composition.

16. The ready to use seed treatment composition of claim 12, wherein the anti-fungal agent is between about 0.05% and about 1.5% by weight of the seed treatment composition.

17. The ready to use seed treatment composition of claim 16, wherein the anti-fungal agent is chitosan.

18. The ready to use seed treatment composition of claim 12, wherein the buffer is between about 0.01% and about 0.5% by weight of the seed treatment composition.

19. The ready to use seed treatment composition of claim 18, wherein the buffer is monobasic potassium phosphate.

\* \* \* \* \*